United States Patent [19]

Dunn

[11] Patent Number: 4,922,898
[45] Date of Patent: May 8, 1990

[54] PROCEDURE FOR VERIFYING PROSTHETIC IMPLANT SEATING

[76] Inventor: Harold K. Dunn, 1231 Chandler Cir., Salt Lake City, Utah 84103

[21] Appl. No.: 252,985

[22] Filed: Oct. 4, 1988

[51] Int. Cl.$^5$ .......................... A61F 5/04; A61F 2/28
[52] U.S. Cl. ........................................ 606/85; 623/66; 623/16; 606/80
[58] Field of Search ........... 128/92 V, 92 VT, 92 VP, 128/92 VJ, 92 VL; 623/16, 18, 20, 22, 23, 66

[56] References Cited

U.S. PATENT DOCUMENTS

| | | | |
|---|---|---|---|
| 4,552,136 | 11/1985 | Kenna | 128/92 VJ |
| 4,576,158 | 3/1986 | Boland | 128/92 VL |
| 4,642,121 | 2/1987 | Kelly | 128/96 VT |

*Primary Examiner*—David J. Isabella
*Attorney, Agent, or Firm*—M. Reid Russell

[57] ABSTRACT

The present invention is in an apparatus and surgical procedure for fitting a hip prosthetic implant to a distal femur in a surgical procedure, replacing the femur neck and ball end. The present process is for testing to verify that a distal femur intramedullary channel is properly prepared to receive, in friction fitting engagement, the prosthetic implant. Which process is practiced utilizing an adapter that is for coupling to a square drive of a torque wrench. In checking for proper intramedullary channel preparation a torsional force is transmitted through the adapter to a rasp seating in the channel, which rasp is used to prepare that intramedullary channel, the torsional force application, to verify proper intramedullary channel preparation, which torque wrench through adapter is also to apply a torsional force to a prosthetic implant seated in that prepared intramedullary channel to verify a proper friction fit thereof.

8 Claims, 2 Drawing Sheets

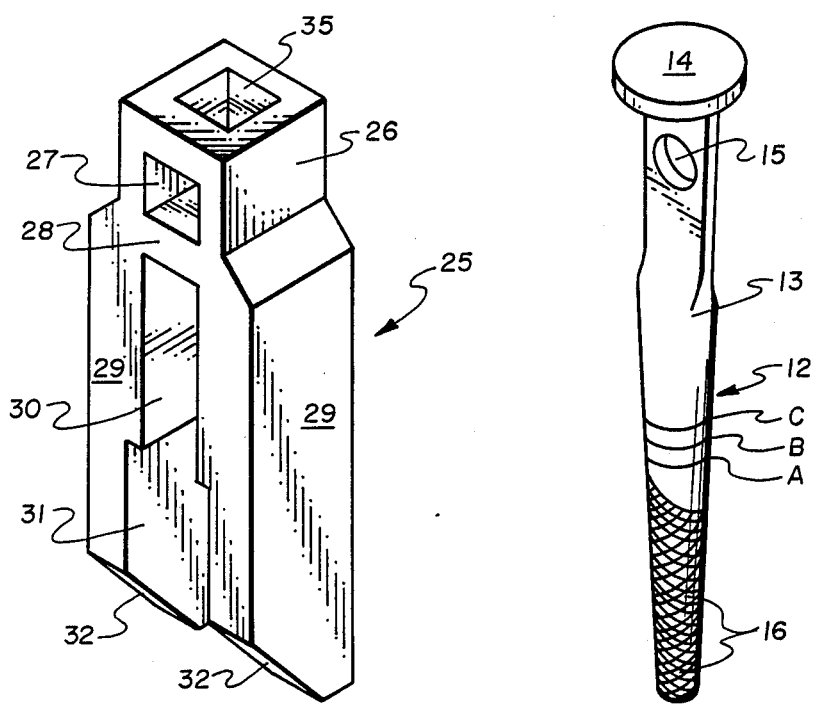
Fig. 3
Fig. 2
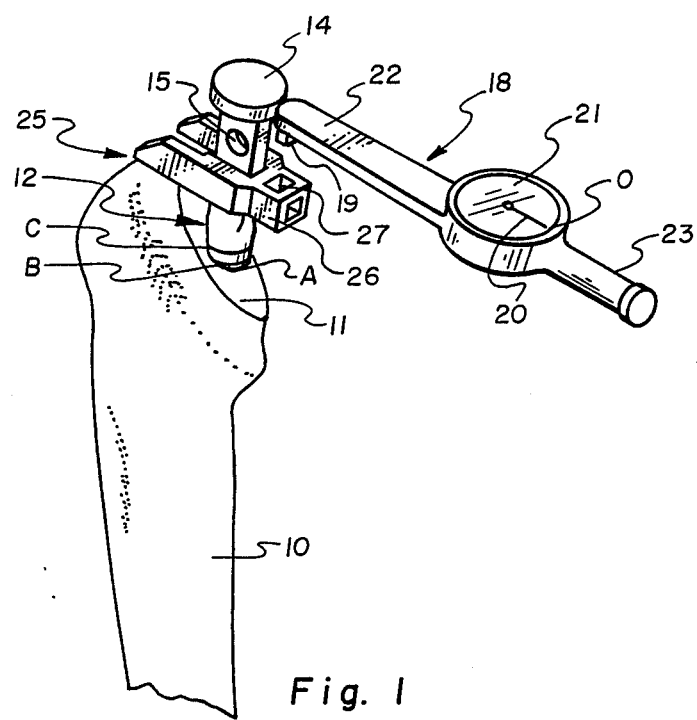
Fig. 1

PROCEDURE FOR VERIFYING PROSTHETIC IMPLANT SEATING

BACKGROUND OF THE INVENTION

1. Field of the Invention

The invention relates generally to surgical instruments and procedures and more particularly to apparatus and a procedure for verifying proper femoral intramedullary channel preparation and seating therein of a prosthetic femoral hip implant.

2. Prior Art

In a hip replacement surgical procedure where the head and neck of the posterior femur are removed and replaced with a prosthetic implant it is required that, once installed, this prosthetic device remain stationary for proper healing and prosthesis functioning. In practice, if a prosthetic implant is loose such that rotational micromovement of the implant within the bone will occur, particularly for a prosthesis that is secured by means of friction or porous ingrowth coatings, that rotational movement will loosen the fit, shearing away the ingrowth, and prohibiting healing.

Accordingly, the present invention is directed to a procedure and apparatus for verifying mechanical fixation of a prosthetic femoral implant during a hip joint replacement surgical procedure.

The present invention involves a system and apparatus for torsionally testing a prosthetic hip implant to verify proper seating. In this procedure, proper seating is assumed where it is determined the implant will maintain stability when subjected to application of a certain torsional force in inch points, as has been determined experimentally. While torsional testing apparatus and procedure have heretofore been practiced in other surgical disciplines, such have not involved prosthetic hip implants. For example, a patent to Boland, U.S. Pat. No. 4,576,158, shows a torsional testing device for testing bone stability; with a patent to Cordey, U.S. Pat. No. 4,359,906, showing a device for tightening a screw into a bone material to a pre-set force; and a patent to Daniel, et al., U.S. Pat. No. 4,712,542, that shows a device and procedure for verifying ligament isometric positioning and tensioning. Where tooling for placing and positioning of certain hip prosthesis are shown in patents to McKee, U.S. Pat. Nos. 3,801,989; Amstutz, 3,857,389; and Kaufer, et al., 3,868,730; these patents do not consider torsional testing of a seated hip femoral prosthesis.

SUMMARY OF THE INVENTION

It is a principal object of the present invention to provide apparatus and a process for torsionally testing to a certain force applied for a period of time to an installed prosthetic hip femoral implant to verify proper seating.

Another object of the present invention is to provide a mechanical system for precisely verifying both proper femoral preparation and torsional stability of a seating prosthetic hip implant.

Still another object of the present invention is to provide apparatus and a process for imparting a certain torsional force for a period of time to a prosthetic hip femoral implant, which force application, provided the implant does not experience rotational micromovement, has been determined in practice will verify proper implant seating.

The present invention is in a procedure and apparatus for use by a surgeon conducting a hip replacement surgical procedure. The procedure is practiced to verify both proper preparation of the femoral intramedullary channel to receive a prosthetic hip femoral implant, and to verify that a seated prosthetic hip femoral implant will not experience rotational micromovement. The apparatus includes a torque wrench to apply, through an adapter, a measured torsional force on a rasp used in preparing the exposed femoral intramedullary channel for testing the seating of prosthetic hip femoral implant. This same torque wrench and adapter is then utilized to verify proper seating of a prosthetic hip femoral implant by applying a determined torsional force to the friction seating prosthetic. For this force application held for a certain time the implant is judged to be properly mechanically fixed in place where it does not experience rotational micromovement as would disrupt porous ingrowth to the implant

BRIEF DESCRIPTION OF THE DRAWINGS

These and other objects and features of the present invention will become more apparent from the following description in which the invention is described in detail in conjunction with the accompanying drawings.

FIG. 1 shows a profile perspective view of the proximal femur wherefrom the head and neck areas, above the lesser trochanter, have been removed and the intramedullary channel prepared to receive a prosthetic implant, which preparation is shown being tested by application of a torsional force through an adapter to a rasp that is shown inserted in that prepared intramedullary channel.

FIG. 2 is an enlarged profile perspective view of the rasp of FIG. 1, removed from the intramedullary channel;

FIG. 3 is an enlarged profile perspective view of the adapter of FIG. 1 rotated to the vertical;

DETAILED DESCRIPTION

Figures 4, 5:
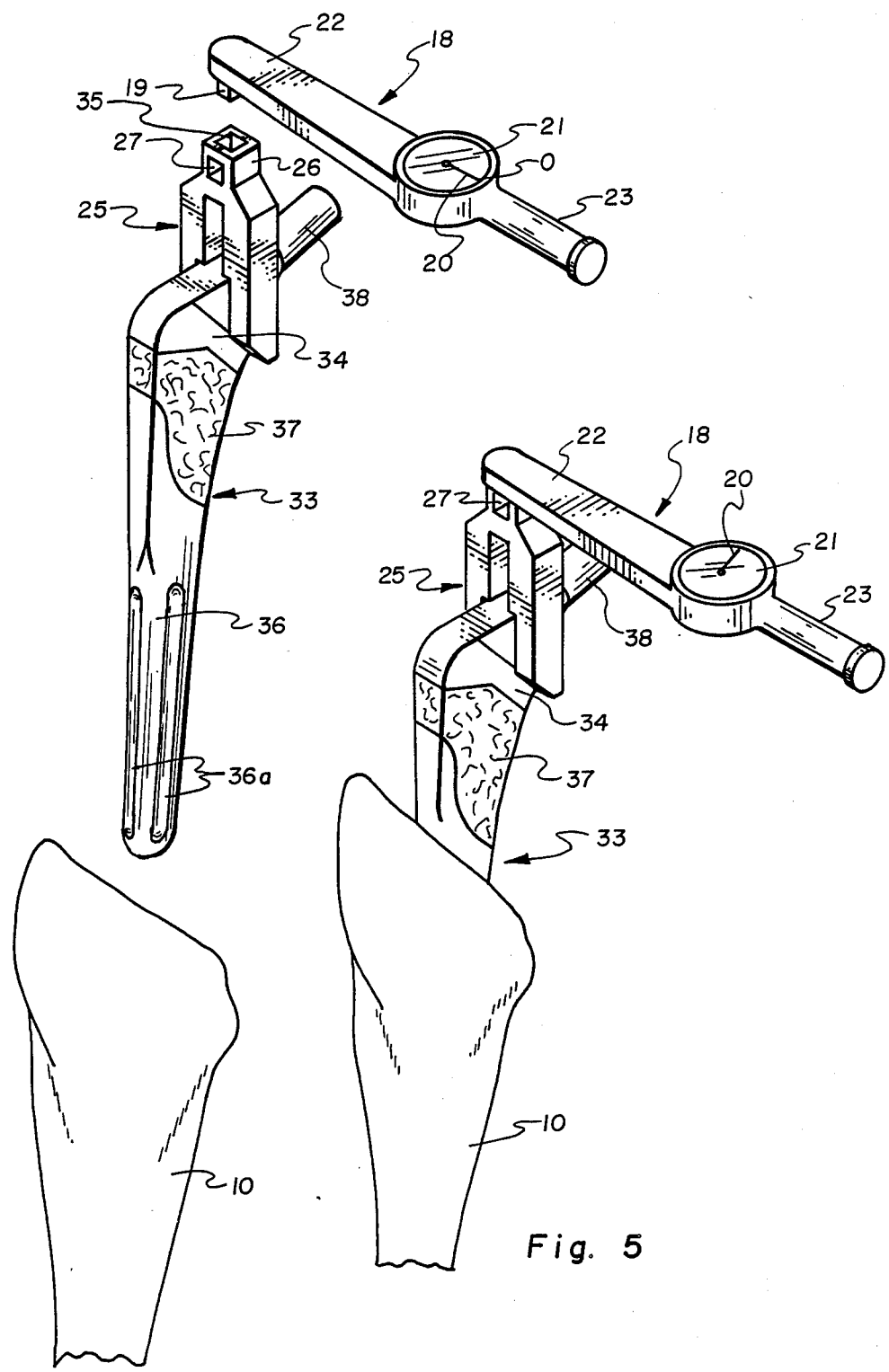
FIG. 4 is a profile perspective view showing the proximal femur of FIG. 1 with a prosthetic hip femoral implant aligned for installation in the prepared intramedullary channel, the adapter of FIG. 3 shown straddling the prosthesis neck with a torque wrench aligned for attachment to that adapter.
FIG. 5 is the assembled view of the components of FIG. 4.

In hip replacement surgery the proximal femur 10, as shown in FIG. 1, is prepared to receive a prosthetic femoral hip implant by cutting the bone along a diagonal across the femur neck, above the lesser and greater trochanter, as shown at 11. The proximal end of the femur intramedullary channel is thereby exposed for enlargement to receive a prosthetic hip femoral implant utilizing a rasp 12. Rasp 12 is shown in FIG. 2 as including, below a flat head end 14 and narrow rectangular portion a body 13, a round cross-section that is tapered inwardly to a blunt lower end. Below the head end 14, in the rectangular portion, the rasp body is holed laterally at 15 to receive a rod or like tool, not shown, that is fitted therethrough for applying a torsional force to the rasp.

FIG. 1 shows the rasp 12 seated in the prepared intramedullary channel end. In that intramedullary channel preparation the rasp is moved up, down and turned therein such that cutting ridges 16, as shown in FIG. 2, will file away the channel wall, appropriately enlarging it to a suitable diameter and depth to accommodate a prosthetic implant like the prosthetic hip implant 33, that is shown in FIGS. 4 and 5. In this filing process, as shown in FIGS. 1 and 2, a force may be applied to the rasp as by tapping it with a hammer, on the rasp head end 14. Which rasp 12, as set out above, can be turned by fitting a rod, not shown, through rasp hole 15, and manually turning it. For preparing the intramedullary channel, the rasp 12 provides, as an arrangement for sizing the channel to a certain opening that will fit a particular size of prosthetic hip implant as determined by the surgeon, lines, shown as A, B and C that are scribed around the rasp mid-portion, as shown in FIGS. 1 and 2. The lines A, B and C represent different sizes of prosthetic hip femoral implants. In practice, the rasp 12 is urged into the intramedullary channel until a select line A, B or C is aligned with the lowest edge of the intramedullary channel, which positioning indicates that the intramedullary channel is appropriately prepared for the particular size of prosthesis.

With the rasp 12 fitted in the intramedullary channel, as set out above, the seating thereof is then torsionally tested. This testing is preferably accomplished utilizing a torque wrench 18 that, as shown in FIGS. 1, 4 and 5, includes a dial 21 for indicating force in points that is applied through a square drive 19. The square drive 19 is operated through an arm, not shown, that is connected to turn a pointer 20 that is pivoted over scale graduations formed around the face of dial 21. The square drive 19, that is journaled in an under surface of housing 22, is arranged to transmit a torque therethrough as applied at a handle end 23 of the torque wrench, which force is displayed as pointer 20 travel over the dial 21 scale graduations. So arranged, the pointer positioning over a scale graduation is indicative of a torquing force being applied through square drive 19. In practice, a dial indicating torque wrench, model "DA", manufactured by Utica Toll Company, Inc., has been used successfully as the torque wrench 18.

Shown in FIG. 1, the torque wrench square drive 19 is aligned to fit into a square opening 28 that is formed in a neck end 26 of an adapter 25. Shown best in FIG. 3, the adapter 25 is preferably formed to have a U-shape with co-planar parallel legs 29 that extend from the ends of a web portion 28. The parallel legs 29 are shown stepped apart from a first narrow opening 30 adjacent to the web portion 28, to second opening 31.

FIG. 1 shows the square drive 19 aligned to enter the adapter square opening 27, which adapter 25 straddles the rectangular cross-section end of the rasp 12. The rasp end is shown seated between the parallel legs 29, and have traveled therein to the first opening 30. So arranged, after the rasp 12 has been used to prepare the bone intramedullary channel for seating a prosthetic implant, a torsional force is applied thereto to verify proper intramedullary channel preparation. In practice, when the rasp 12 does not experience rotational micromovement at an applied torque of approximately sixty (60) inch pounds applied for approximately fifteen (15) seconds it can be assumed that the intramedullary channel is properly prepared to receive the prosthetic hip femoral implant 33 seated therein.

Shown in FIG. 4, the prosthetic hip femoral implant 33, hereinafter referred to as implant, is aligned for installation in the prepared intramedullary channel and has the adapter 25 fitted over a neck 34 thereof. The preferred implant neck 34 is of a thickness to just fit between the parallel legs 29 at the second opening, the area between the second and first openings to butt against a top surface of that neck. As shown in FIG. 1, the adapter parallel legs 29 has sloped ends 32 that butt against an upper edge of a compressed metal shavings matt 37 that is arranged as a mid-section of the implant, below a dogleg bend, hereinafter referred to as matt 37. Matt 37 is to provide an area of multiple ridges and depressions for encouraging bone growth into the matt as will occur in the natural healing process.

Shown best in FIG. 4, the prosthetic implant edges, below matt 37 are curved to essentially a round cross-section, of a bottom portion 36. The implant bottom portion includes elongate depressions 36a that are formed in opposite surfaces thereof that are for receiving bone growth therein to further lock the implant in place.

FIG. 4 shows the wrench square drive 19 aligned for fitting in a second square opening 35 of the adapter 25, which square opening 35 is longitudinally formed into the adapter neck 26, at a right angle to the square opening 27. In FIG. 5 the torque wrench 18 is shown connected through adapter 25 to apply a torsional force to the implant 33, after which implant has been seated in the prepared intramedullary channel. Whereafter a ball, not shown, of a ball and socket hip joint prosthesis can be secured to the implant head end shaft 38.

FIG. 5 shows the torque wrench 18 with its square drive 19 connected to the adapter 25 at the second square opening 35. So arranged, the adapter parallel legs 29 straddle the implant 33 to impart a torsional force thereto as reflected by the positioning of pointer 20 over one of the scale graduations of dial 21. In practice, the implant 33 is secured by its friction engagement in the prepared intramedullary channel. With bone growth to the implant as occurs in the healing process to further secure the implant in place. Should, however, that implant, after seating, be subject to rotational movement, that movement will tend to shear away the porous bone ingrowth, tending to loosen the friction fit, destabilizing the appliance. Accordingly, it is highly desirable to test implant seating prior to closure. The present invention provides for such testing by the application of a torsional force of approximately sixty (60) inch pounds for approximately fifteen (15) seconds thereto. At such force application, if the appliance does not experience rotational micromovement, the implant friction fit can be judged to be secure. Providing, of course, the implant 33 is otherwise stable. The applied force can vary for different sizes of implants and accordingly, for a full range of sizes of a preferred prosthetic implant identified as an "Anatomic Hip", manufactured by Zimmer, Inc., the torsional force to be applied to confirm an acceptable friction fit is approximately sixty (60) inch pounds of torque, plus or minus ten (10) pounds for fifteen (15) seconds, plus or minus five (5) seconds. Of course, a greater force application for a longer period of time can obviously be used within the scope of this disclosure.

Hereinabove has been set out a preferred system and apparatus of the present invention for practicing a torsional testing process to verify a proper friction mounting of a hip prosthetic implant. It should, however, be understood that the present disclosure is made by way of example only and that the apparatus and process set out herein may be varied without departing from the subject matter coming within the scope of the following claims, and any reasonable equivalency thereof, which claims I regard as my invention.

I claim:

1. A process for verifying proper friction coupling of a prosthetic hip implant in a prepared femoral intramedullary channel comprising the steps of, to a proximal femur that has had the head and neck thereof removed along a diagonal above the greater and lesser trochanter, preparing the intramedullary channel to receive a prosthetic hip implant; seating a rasp tool means in the prepared intramedullary channel; applying a torsional force to said rasp tool means for a period of seconds where, if said rasp tool means does not experience rotational micromovement, the intramedullary channel preparation is deemed to be correct; installing a prosthetic hip implant in friction fitting engagement in said prepared intramedullary channel; testing the friction fit of said prosthetic hip implant by applying a torsional force for a period of seconds on said prosthetic hip implant, with the fit determined to be correct if said prosthetic hip implant does not experience rotational micromovement.

2. In a process as recited in claim 1, wherein the torsional force applied to both the rasp tool means and prosthetic hip implant is approximately sixty (60) inch pounds, plus or minus ten (10) inch pounds.

3. A process as recited in claim 1, wherein the torsional force applied to both the rasp tool means and prosthetic hip implant is applied for approximately fifteen (15) seconds, plus or minus five (5) seconds.

4. A process as recited in claim 1, wherein the torsional force is applied through an adapter by a torque wrench having a capability to visually display the force being applied therethrough.

5. A process for verifying adequate bone removal from a femur intramedullary channel in preparation for implantation of a femoral component of a hip prosthesis comprising the steps of, resecting a natural femoral head from a femur so as to expose the intramedullary channel; fitting a selected rasp tool means into said intramedullary channel; attaching a means for applying a torque to said rasp tool means; and applying a torsional force to said rasp tool means through said attaching means of a magnitude to where an absence of rotational micromovement of said rasp tool means within said intramedullary channel verifies adequate bone removal.

6. A process as recited in claim 5, wherein the torsional force applied to said rasp tool means is sixty (60) inch pounds, plus or minus ten (10) inch pounds.

7. A process as recited in claim 5, wherein the torsional force is applied to said rasp tool means for fifteen (15) seconds, plus or minus five (5) seconds.

8. A process as recited in claim 5, wherein the torsional force is applied through an adapter by a torque wrench that includes a visual display showing a force being applied therethrough.

* * * * *